United States Patent

Schulz et al.

Patent Number: 5,244,476
Date of Patent: Sep. 14, 1993

[54] BENZOPHENONE ETHER ESTERS, PROCESSES FOR THEIR PREPARATION, AND THEIR USE FOR IMPROVING THE LIGHT STABILITY OF POLYESTER DYEINGS

[75] Inventors: Joachim Schulz, Pohle; Günter Bartels, Burgwedel, both of Fed. Rep. of Germany

[73] Assignee: Cassella AG, Frankfurt, Fed. Rep. of Germany

[21] Appl. No.: 838,765

[22] PCT Filed: Sep. 6, 1990

[86] PCT No.: PCT/EP90/01493

§ 371 Date: Mar. 13, 1992

§ 102(e) Date: Mar. 13, 1992

[87] PCT Pub. No.: WO91/04243

PCT Pub. Date: Apr. 4, 1991

[30] Foreign Application Priority Data

Sep. 13, 1989 [DE] Fed. Rep. of Germany ....... 3930516

[51] Int. Cl.$^5$ .................. C07C 69/14; C07C 69/54; C07C 69/78; D06P 1/64

[52] U.S. Cl. .................................... 8/442; 8/490; 8/524; 8/527; 8/607; 8/609; 8/610; 8/922

[58] Field of Search .................. 8/442, 490, 524, 607, 8/609, 610, 527

[56] References Cited

U.S. PATENT DOCUMENTS

| | | | |
|---|---|---|---|
| 4,789,382 | 12/1988 | Neumann et al. | 8/442 |
| 4,824,892 | 4/1989 | Eiglmeier et al. | 252/407 |
| 4,911,732 | 3/1990 | Neumann et al. | 8/442 |

Primary Examiner—A. Lionel Clingman
Attorney, Agent, or Firm—Connolly and Hutz

[57] ABSTRACT

The present invention relates to compounds of the general formula I

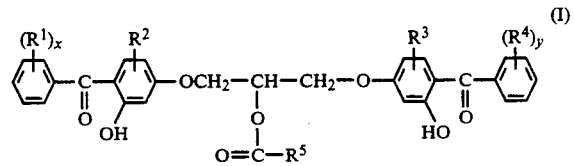

in which $R^1$, $R^2$, $R^3$, $R^4$, $R^5$, x and y are defined as in the description, processes for their preparation, their use for improving the light stability of polyester dyeings and a dyeing process and dye preparations.

8 Claims, No Drawings

BENZOPHENONE ETHER ESTERS, PROCESSES FOR THEIR PREPARATION, AND THEIR USE FOR IMPROVING THE LIGHT STABILITY OF POLYESTER DYEINGS

The present invention relates to benzophenone ether esters, processes for their preparation, their use for improving the light stability of polyester dyeings and a dyeing process and dye preparations.

A process for improving the light fastness of polyester dyeings, in which alkyl ethers of 2,2',4,4'-tetrahydroxybenzophenone are used, has already been described in DE-AS 11 56 760. However, this process has a number of disadvantages. Thus, in the case of bright dyeings, the hue is shifted and the brilliance is reduced to a greater or lesser degree. The dyes do not show sufficiently good exhaustion onto the fiber, resulting in wastewater problems. Furthermore, the benzophenone derivatives described there have a tendency to migrate during the customary exposure to dry heat setting.

Processes for improving the light fastness of polyester dyeings using certain benzophenone ether esters have also already been disclosed in EP-A 254 987 and EP-A 309 909.

Furthermore, benzophenone ether esters which are used for protecting plastics, such as, for example, polyacrylic esters, polymethacrylic esters, polystyrene and ABS polymers, against the effect of UV light are disclosed in EP 182 056.

The object of the present invention is to provide compounds which lead to an improvement in the light fastness of dyeings on polyester materials, without reduction in the exhaustion of the dye onto the fiber and the depth of shade and brilliance of the dyeing.

Surprisingly, this object is achieved by compounds of the general formula I

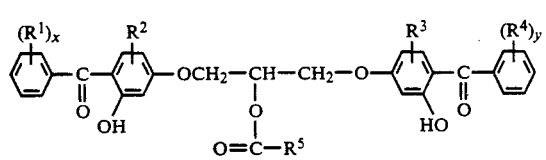

in which $R^1$ and $R^4$, independently of one another, are $(C_1-C_6)$-alkyl, cyano, fluorine, chlorine, bromine, trifluoromethyl or hydrogen;

$R^2$ and $R^3$, independently of one another, are $(C_1-C_6)$-alkyl or hydrogen;

x and y, independently of one another, are 0, 1 or 2 and $R^5$ represents $(C_1-C_{12})$-alkyl; $(C_3-C_8)$-cycloalkyl; $(C_1-C_{12})$-alkyl or $(C_3-C_8)$-cycloalkyl, each of which is substituted by $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro; phenyl or phenyl substituted by $(C_1-C_6)$-alkyl, $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro.

The alkyl, alkoxy, alkoxycarbonyl, alkylamino and dialkylamino radicals can be straight-chain or branched.

The radicals $R^1$ and $R^4$ can be in the ortho, meta or para position relative to the carbonyl group. Where x or y is 2, the substituents can be in the 1,2-, 1,3- or 1,4-position relative to one another.

The radicals $R^2$ and $R^3$ can be bound to all three free positions of the six-membered ring.

Preference is given to compounds of the general formula I in which $R^1$ and $R^4$, independently of one another, are hydrogen, $(C_1-C_3)$-alkyl, cyano, chlorine or trifluoromethyl, $R^2$ and $R^3$, independently of one another, are hydrogen or $(C_1-C_3)$-alkyl, x and y, independently of one another, are 0 or 1 and $R^5$ is $(C_1-C_4)$-alkyl; cyclopentyl, cyclohexyl; $(C_1-C_4)$-alkyl, cyclopentyl or cyclohexyl, each of which is substituted by $(C_1-C_4)$-alkoxy, $(C_2-C_5)$-alkoxycarbonyl, amino, $(C_1-C_4)$-alkylamino, di-$(C_1-C_4)$-alkylamino, hydroxyl, cyano, fluorine, chlorine, bromine, trifluoromethyl or nitro; phenyl or phenyl which is substituted by $(C_1-C_4)$-alkyl, $(C_1-C_4)$-alkoxy, $(C_2-C_5)$-alkoxycarbonyl, amino, $(C_1-C_{14})$-alkylamino, di-$(C_1-C_4)$-alkylamino, hydroxyl, cyano, fluorine, chlorine, bromine, trifluoromethyl or nitro.

Particular preference is given to compounds of the general formula I in which $R^1$, $R^2$, $R^3$ and $R^4$ are hydrogen, x and y are 0 and $R^5$ is methyl or phenyl.

The compounds according to the invention of the general formula I can be prepared by reacting a compound of the general formula II

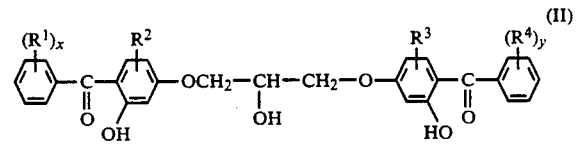

in which $R^1$, $R^2$, $R^3$, $R^4$, x and y are as defined above, with a compound of the general formula III

in which X represents hydroxyl, halogen, $(C_1-C_4)$-alkoxy or —$OCOR^5$ and $R^5$ is as defined above.

The reaction is advantageously carried out at temperatures of 0° to 150° C., particularly preferably at 50° to 120° C.

Preferably, the reaction is carried out in an inert organic solvent. Suitable solvents of this type are in particular aromatic hydrocarbons having 6 to 8 carbon atoms, which may be substituted by a halogen atom, for example by a chlorine atom, or aliphatic halohydrocarbons, for example chlorohydrocarbons having 1 to 2 carbon atoms. Particularly preferred solvents are benzene, toluene, xylene, chlorobenzene, chloroform, tetrachloromethane and 1,2-dichloroethane.

The solvent is preferably used in amounts of 1 to 10 liters, particularly preferably 5 to 8 liters, per mole of the compound of the general formula I.

It is particularly advantageous to carry out the reaction in the presence of an acid catalyst, an inorganic or organic acid being particularly suitable. Organic sulfonic acids, such as, for example, p-toluenesulfonic acid, are preferred. Organic sulfonic acids containing halogen atoms, in particular fluorine atoms, such as, for example, trifluoromethanesulfonic acid, are par-ticularly preferred. Acid ion exchangers are also suitable as acid catalysts.

The catalyst is preferably used in an amount of 1 to 10, particularly preferably 3 to 6, percent by weight, relative to the compound of the general formula II.

The compound of the general formula III is preferably used in an excess of up to 10 mol per mole of compound of the general formula II. An excess of 3 to 8 mol is particularly preferred.

The compounds of the general formula III are carboxylic acids or carboxylic acid derivatives which are commercially available and/or preparable by methods known to one skilled in the art. Examples of carboxylic acids of this type are aliphatic carboxylic acids, such as acetic acid, propionic acid or butyric acid and aromatic carboxylic acids, such as benzoic acid.

Likewise, the compounds of the general formula I are known from the literature (see, for example CA 86(1977) 106170 t).

The compounds according to the invention are highly suitable for improving the light fastness of polyester dyeings. Surprisingly, it has now been found that the compounds of the general formula I which have already been disclosed in EP 182 056 and are preparable by the processes described there, in which $R^5$ is a group of the general formula A $$-\underset{R^6}{\overset{|}{C}}=C\overset{R^7}{\underset{R^8}{\diagdown}} \quad (A)$$

in which
$R^6$ is hydrogen, phenyl, $(C_1-C_{12})$-alkyl or cyano and $R^7$ and $R^8$, independently of one another, are hydrogen, $(C_1-C_8)$-alkyl, phenyl or phenyl substituted by $(C_1-C_4)$-alkyl or $(C_1-C_4)$-alkoxy or together form an alkylene radical having 4 or 5 carbon atoms, are highly suitable for this purpose.

Accordingly, the present invention also relates to the use of a compound of the general formula I $$(R^1)_x \underset{OH}{\overset{R^2}{\diagdown}} \underset{}{\overset{}{\diagdown}} -OCH_2-CH-CH_2-O-\underset{HO}{\overset{R^3}{\diagdown}} \underset{}{\overset{(R^4)_y}{\diagdown}} \quad (I)$$
$$\overset{|}{O=C-R^5}$$

in which $R^1$ and $R^4$, independently of one another, are $(C_1-C_6)$-alkyl, cyano, fluorine, chlorine, bromine, trifluoromethyl or hydrogen;
$R^2$ and $R^3$, independently of one another, are $(C_1-C_6)$-alkyl or hydrogen;
x and y, independently of one another, are 0, 1 or 2 and
$R^5$ represents $(C_1-C_{12})$-alkyl; $(C_3-C_8)$-cycloalkyl; $(C_1-C_{12})$-alkyl or $(C_3-C_8)$-cycloalkyl, each of which is substituted by $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro; phenyl or phenyl substituted by $(C_1-C_6)$-alkyl, $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro, or a group of the general formula A $$-\underset{R^6}{\overset{|}{C}}=C\overset{R^7}{\underset{R^8}{\diagdown}} \quad (A)$$

in which
$R^6$ is hydrogen, phenyl, $(C_1-C_{12})$-alkyl or cyano and $R^7$ and $R^8$, independently of one another, are hydrogen, $(C_1-C_8)$-alkyl, phenyl or phenyl substituted by $(C_1-C_4)$-alkyl or $(C_1-C_4)$-alkoxy or together form an alkylene radical having 4 or 5 carbon atoms, for improving the light fastness of polyester dyeings.

It is particularly advantageous if the compounds of the general formula I are already used during dyeing, i.e. are present in the dye bath. Accordingly, the present invention also relates to a process for the dyeing of textile polyester material using disperse dyes, characterized in that the dye bath contains, for improving the light fastness of the dyeing, at least one compound of the general formula I, not only the compounds according to the invention of the general formula I but also the compounds of the general formula I disclosed in EP 182 056, in which $R^5$ represents the group A, being included.

Textile polyester material is understood to mean in particular structures such as, for example, fibers, yarns, woven fabrics, knitted fabrics and films made of, for example, polyethylene terephthalates, polybutylene terephthalates or polyethylene glycol terephthalates. The disperse dyes used are preferably commercially available disperse dyes, such as, for example, azo, anthroquinone, methine, quinophthalone or coumarin dyes.

Dyeing can take place, for example, by the so-called exhaust method under HT conditions, at the boiling temperature with the addition of carrier or even by the so-called thermosol method. The dyeing processes mentioned are known to one skilled in the art and described in the relevant literature.

The dye baths contain the compounds of the general formula I in amounts of preferably 0.1 to 10, particularly preferably 0.3 to 5, percent by weight, relative to the textile material to be dyed.

The compounds of the general formula I can be added to the dye baths, for example, as powders, spray-dried/redispersible, or as liquid preparation in the form of a dispersion.

However, particularly preferably, the compounds of the general formula I are already present in the dye preparations from which the dye baths are produced.

Accordingly, the present invention also relates to a dye preparation characterized in that it contains at least one compound of the general formula I, not only the compounds according to the invention of the general formula I but also the compounds of the general formula I disclosed in EP 182 056, in which $R^5$ represents the group A, being included.

The dye preparations according to the invention are liquid or pulverulent disperse dye preparations containing the compounds of the general formula I preferably in amounts of 1 to 50 percent by weight, particularly preferably 1 to 30 percent by weight. The dye content is preferably 15–40 percent by weight, particularly preferably 20–30 percent by weight.

The dye preparations are prepared by milling the dye in the presence of one or more compounds of the general formula I, one or more dispersants or one or more emulsifiers and, if desired, in the presence of further auxiliaries together in suitable mills.

Examples of suitable mills are ball or sand mills.

The milling process is carried out at 0° to 100° C., preferably at 20° to 70° C.

If it is desired to prepare a pulverulent dispersion, the milling process must be followed by spray-drying.

In the case of liquid preparations, the compounds of the general formula I can also be added after milling, provided they are thoroughly stirred in. Examples of suitable dispersants are anionic or nonionic dispersants, which may also be used together. Examples of anionic dispersants are condensation products of aromatic sulfonic acids with formaldehyde, in particular condensation products of alkylnaphthalenesulfonic acids with formaldehyde, condensation products of substituted or unsubstituted phenol, naphthalene- or naphtholsulfonic acids with formaldehyde and sodium bisulfite, alkali metal salts of condensation products with formaldehyde and urea and alkali metal salts of lignosulfonic acids. Alkyl- or alkylarylsulfonates and alkylarylpolyglycol ether sulfates and in particular neutralized esters of an oxethylated novolak. Examples of nonionic dispersants or emulsifiers are ethylene oxide or propylene oxide together with alkylatable compounds, such as, for example, fatty alcohols, fatty amines, fatty acids, phenols, alkylphenols, arylalkylphenols, arylalkylarylphenols and carboxamides, such as, for example, addition products of 5 to 10 ethylene oxide units with $C_8$–$C_{10}$-alkylphenols.

The dispersants mentioned are present in liquid dye preparations in an amount of 15–40 percent by weight, preferably 20–30 percent by weight, and in pulverulent dye preparations in an amount of 20–45% by weight.

The dye preparations according to the invention can also contain further auxiliaries, for example those acting as oxidizing agents, such as, for example, sodium m-nitrobenzenesulfonate or fungicides, such as, for example, sodium o-phenolphenolate[sic] and sodium pentachlorophenolate. Dye mixtures which are formulated as powders moreover additionally contain other auxiliaries, such as, for example, wetting or dedusting agents. The dye preparations contain the auxiliaries mentioned in amounts of 0–5 percent by weight, preferably 0–2 percent by weight.

Dyeings which are obtained by the dyeing process according to the invention, i.e. in the presence of compounds of the general formula I, do not differ or differ only insignificantly from those obtained without addition of the compounds of the general formula I with respect to their hue. However, they are distinguished by a substantially higher light fastness, in particular also hot light fastness. Thus, even the high demands made on dyeings in the automotive sector (seat covers, parcel shelves, and the like) are met and even exceeded.

EXAMPLE 1

(1,3-bis(4-Benzoyl-3-hydroxyphenoxy)-2-propyl methacrylate a) Synthesis

A solution of 97 g (0.2 mol) of 1,3-bis(4-benzoyl-3-hydroxyphenoxy)-2-propanol and 103 g (1.2 mol) of methacrylic acid in 1200 ml of toluene were heated, after the addition of 6 g of trifluoromethanesulfonic acid, 0.2 g of hydroquinone and 0.2 g of hydroquinone monomethyl ether, at a temperature of 105° to 110° C. for 3 hours. After cooling to room temperature, the reaction mixture was washed with 3 l of water. The toluene was then distilled off from the reaction mixture at a pressure of 20 mbar. The remaining oily residue was dissolved in hot ethanol. Cooling of this solution to room temperature gave 86 g (78% of theory) of (1,3-bis(4-benzoyl-3-hydroxy)-2-propyl) methacrylate in the form of colorless crystals having a melting point of 138° to 139° C. and a purity of 99% (HPLC). The UV spectrum gave two absorption maxima at wavelengths of 287 nm (absorbance of 0.517; extinction coefficient 28570) and 324 nm (absorbance of 0.333; extinction coefficient 18400).

b) Dyeing

A dye bath comprising 1500 parts of water, 0.6 part of a dye mixture of
a) a yellow mixture of 0.08 part of Disperse Yellow 42, 0.08 part of Disperse Yellow 86, 0.08 part of Disperse Yellow 108,
b) a red mixture of 0.035 part of Disperse Red 91, 0.035 part of Disperse Red 92, 0.035 part of Disperse Red 279,
c) a blue mixture of 0.091 part of Disperse Blue 77, 0.091 part of Disperse Blue 56, 0.091 part of Disperse Blue 27, 2 parts of ®Dispersogen A (dispersant from Hoechst AG, Frankfurt, West Germany) and 1.5 parts of the compound from a) is brought to a pH of 4.5–5 with acetic acid.

Starting at 60° C., 100 parts of a polyester yarn are dyed in this dye bath using an HT dyeing apparatus. The temperature is increased to 135° C. over a period of 30 minutes, and dyeing is continued at 135° C. for another 90 minutes. This gives a light gray dyeing which reaches significantly better light fastnesses in an exposure in the xenon test under the conditions according to DIN 75202 than a dyeing without addition of the compound from a).

EXAMPLE 2

(1,3-bis(4-Benzoyl-3-hydroxyphenoxy)-2-propyl acetic acid radicals a) Synthesis

A solution of 484 g (1 mol) of 1,3-bis(4-benzoyl-2-hydroxyphenoxy)-2-propanol and 360.3 g (6 mol) of acetic acid in 2.6 l of toluene was heated, after addition of 6 g of trifluoromethanesulfonic acid and 5 g of methanesulfonic acid, to reflux in a water separator for 5 hours until, by separation of the calculated amount of water—18 g—the reaction is complete. After cooling to room temperature, the reaction mixture was washed with 5 l of water. The toluene was then distilled off from the reaction mixture at a pressure of about 20 mbar. For purification, the remaining residue was dissolved in a hot mixture consisting of acetone/ethanol.

Cooling of this solution to 15° C. gave 421 g (80% of theory) of (1,3-bis(4-benzoyl-2-hydroxyphenoxy)-2-propanol) acetate in the form of fine colorless crystals and a purity of 99% (HPLC). UV, IR and NMR spectra correspond to the compound mentioned.

b) Dyeing 100 parts of a polyester velour are dyed in a dye bath which is analogous to that from Example 1b) but contains 1.5 parts of the compound from Example 2a) and a dye mixture of 0.43 part of Disperse Yellow 51, 0.46 part of a red mixture as in Example 1b) and 0.17 part of Disperse Blue 77.

This gives an off-pink dyeing which reaches significantly better light fastness in exposure under the conditions according to DIN 75202 than a dyeing without addition of the compound from Example 2a).

EXAMPLE 3

(1,3-bis(4-Benzoyl-3-hydroxyphenoxy)-2-propyl) benzoate.

a) Synthesis 141 g (1 mol) of benzoyl chloride were added to a solution of 200 g (0.41 mol) of 1,3-bis(4-benzoyl-3-hydroxyphenoxy)-2-propanyl[sic] and 80 g of pyridine at a temperature of 100° to 105° C. over a period of 3 hours. A fine precipitate of pyridine hydrochloride formed in the clear solution. The reaction was completed at 100°–105° C. for another 3 hours. After cooling to room temperature, the reaction mixture was washed with 2 l of water. The toluene was then distilled off from the reaction mixture at a pressure of about 20 mbar. The remaining residue was purified by recrystallization.

The product thus obtained has a melting point of 168°–169° C. and a purity of 99% (HPLC). UV, IR and NMR spectra correspond to the compound mentioned.

b) Dyeing 100 parts of a polyester knitted fabric are dyed in a dye bath analogous to that from Example 1b) but containing 2 parts of the compound from Example 3a) and a dye mixture of 0.46 part of Disperse Yellow 42, 0.17 part of a red mixture as in Example 1b) and 0.17 part of a blue mixture as in Example 1b).

This gives a beige dyeing which, when exposed according to DIN 75202, reaches a significantly better light fastness than a comparable dyeing without addition of the compound from Example 3a).

We claim:

1. Process for the dyeing of textile polyester material using disperse dyes, characterized in that the dye bath contains, for improving the light fastness of the dyeing, at least one compound of the general formula I

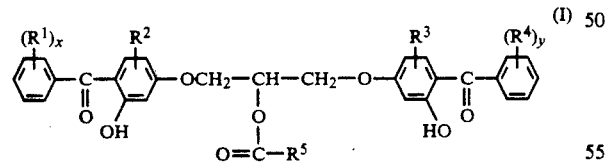

in which $R^1$ and $R^4$, independently of one another, are $(C_1-C_6)$-alkyl, cyano, fluorine, chlorine, bromine, trifluoromethyl or hydrogen;

$R^2$ and $R^3$, independently of one another, re $(C_1-C_6)$-alkyl or hydrogen;

x and y, independently of one another, are 0, 1 or 2 and $R^5$ represents $(C_1-C_{12})$-alkyl; $(C_3-C_8)$-cycloalkyl; $(C_1-C_{12})$-alkyl or $(C_1-C_8)$-cycloalkyl, each of which is substituted by $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro; phenyl or phenyl substituted by $(C_1-C_6)$-alkyl, $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro, or a group of the general formula A

in which $R^6$ is hydrogen, phenyl, $(C_1-C_{12})$-alkyl or cyano and $R^7$ and $R^8$, independently of one another, are hydrogen, $(C_1-C_8)$-alkyl, phenyl or phenyl substituted by $(C_1-C_4)$-alkyl or $(C_1-C_4)$-alkoxy or together form an alkylene radical having 4 or 5 carbon atoms.

2. Process according to claim 1, characterized in that the dye bath contains the compound of the general formula I in amounts of 0.1 to 10 percent by weight, relative to the textile material to be dyed.

3. Process according to claim 2, characterized in that the dye bath contains the compound of the general formula I in amounts of 0.3 to 5 percent by weight, relative to the textile material to be dyed.

4. A process for dyeing using dispersed dyes comprising using a compound of the general formula I

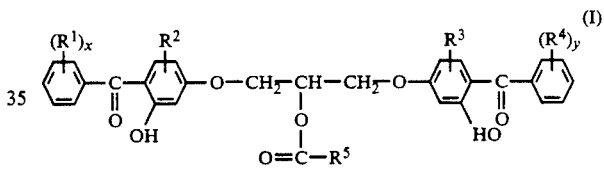

in which $R^1$ and $R^4$, independently of one another, are $(C_1-C_6)$-alkyl, cyano, fluorine, chlorine, bromine, trifluoromethyl or hydrogen;

$R^2$ and $R^3$, independently of one another, are $(C_1-C_6)$-alkyl or hydrogen;

x and y, independently of one another, are 0, 1 or 2 and $R^5$ represents $(C_1-C_{12})$-alkyl; $(C_3-C_8)$-cycloalkyl; $(C_1-C_{12})$-alkyl or $(C_3-C_8)$-cycloalkyl, each of which is substituted by $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro; phenyl or phenyl substituted by $(C_1-C_6)$-alkyl, $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro for improving the light fastness of polyester dyeings.

5. A process for dyeing using dispersed dyes comprising using a compound of the general formula I

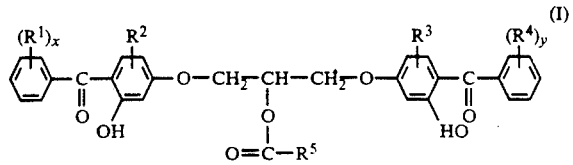

in which $R^1$ and $R^4$, independently of one another, are $(C_1-C_6)$-alkyl, cyano, fluorine, chlorine, bromine, trifluoromethyl or hydrogen;

$R^2$ and $R^3$, independently of one another, are $(C_1-C_6)$-alkyl or hydrogen;

x and y, independently of one another, are 0, 1 or 2 and $R^5$ represents $(C_1-C_{12})$-alkyl; $(C_3-C_8)$-cycloalkyl; $(C_1-C_{12})$-alkyl or $(C_3-C_8)$-cycloalkyl, each of which is substituted by $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro; phenyl or phenyl substituted by $(C_1 14 \ C_6)$-alkyl, $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro, or a group of the general formula A

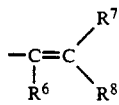

in which $R^6$ is hydrogen, phenyl, $(C_1-C_{12})$-alkyl or cyano and $R^7$ and $R^8$, independently of one another, are hydrogen, $(C_1-C_8)$-alkyl, phenyl or phenyl substituted by $(C_1-C_4)$-alkyl or $(C_1-C_4)$-alkoxy or together form an alkylene radical having 4 to 5 carbon atoms, for improving the light fastness of polyester dyeings.

6. Dispersed dye preparations characterized in that it contains at least one compound of the general formula I

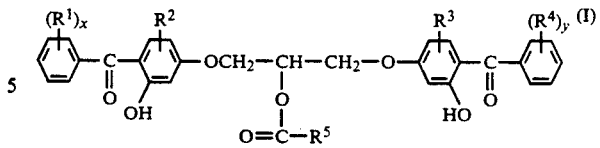

in which $R^1$ and $R^4$, independently of one another, are $(C_1-C_6)$-alkyl, cyano, fluorine, chlorine, bromine, trifluoromethyl or hydrogen;

$R^2$ and $R^3$, independently of one another, are $(C_1-C_6)$-alkyl or hydrogen;

x and y, independently of one another, are 0, 1 or 2 and $R^5$ represents $(C_1-C_{12})$-alkyl; $(C_3-C_8)$-cycloalkyl; $(C_1-C_{12})$-alkyl or $(C_3-C_8)$-cycloalkyl, each of which is substituted by $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro; phenyl or phenyl substituted by $(C_1-C_6)$-alkyl, $(C_1-C_6)$-alkoxy, $(C_2-C_7)$-alkoxycarbonyl, amino, $(C_1-C_6)$-alkylamino, di-$(C_1-C_6)$-alkylamino, hydroxyl, cyano, fluorine, chlorine, bromine, trifluoromethyl or nitro, or a group of the general formula A $$-\underset{R^6}{\overset{R^7}{C}}=C\underset{R^8}{\diagdown} \quad (A)$$

in which $R^6$ is hydrogen, phenyl, $(C-C_{12})$-alkyl or cyano and $R^7$ and $R^8$, independently of one another, are hydrogen, $(C_1-C_8)$-alkyl, phenyl or phenyl substituted by $(C_1-C_4)$-alkyl or $(C_1-C_4)$-alkoxy or together form an alkylene radical having 4 or 5 carbon atoms.

7. Dispersed dye preparations according to claim 6, characterized in that it contains the compounds of the general formula I in amounts of 1 to 50 percent by weight.

8. Dye preparation according to claim 7, characterized in that it contains the compounds of the general formula I in amounts of 1 to 30 percent by weight.

* * * * *